United States Patent
Thoonen et al.

(10) Patent No.: US 6,768,017 B2
(45) Date of Patent: Jul. 27, 2004

(54) PROCESS FOR THE PRODUCTION OF MONOALKYLTIN TRIHALIDES

(75) Inventors: Sander Thoonen, Utrecht (NL); Gerard van Koten, Den Dolder (NL); Berth Jan Deelman, Kapelle (NL)

(73) Assignee: Atofina Vlissingen B.V., Vlissingen-Oost (NL)

( * ) Notice: Subject to any disclaimer, the term of this patent is extended or adjusted under 35 U.S.C. 154(b) by 0 days.

(21) Appl. No.: 10/466,702

(22) PCT Filed: Jan. 21, 2002

(86) PCT No.: PCT/NL02/00045

§ 371 (c)(1),
(2), (4) Date: Dec. 8, 2003

(87) PCT Pub. No.: WO02/057277

PCT Pub. Date: Jul. 25, 2002

(65) Prior Publication Data

US 2004/0077891 A1 Apr. 22, 2004

(30) Foreign Application Priority Data

Jan. 19, 2001 (EP) ............................................ 01200209

(51) Int. Cl.$^7$ .............................. C07F 7/22; B01J 31/00
(52) U.S. Cl. .............................. 556/97; 556/21; 556/95; 556/136; 556/137; 502/152; 502/155
(58) Field of Search ............................... 556/21, 95, 97, 556/136, 137; 502/152, 155

(56) References Cited

U.S. PATENT DOCUMENTS

| 3,454,610 A | * | 7/1969 | Langer ........................ 556/85 |
| 3,862,198 A | * | 1/1975 | Kugele et al. ................. 556/97 |
| 4,148,814 A | * | 4/1979 | Reifenberg .................... 556/97 |
| 4,604,475 A | * | 8/1986 | Buschhoff et al. ............. 556/97 |

* cited by examiner

Primary Examiner—Porfirio Nazario-Gonzalez
(74) Attorney, Agent, or Firm—Hoffmann & Baron, LLP

(57) ABSTRACT

The present invention is directed to a process for the production of monoalkylin trihalides of the formula $RSnX_3$ wherein R-alkyl or cycloalkyl and X—Cl, Br or I involving a redistribution reaction between tetraorganotins, triorganotin halides or diorganotin halides and tin tetrahalides, said process comprising contacting tetra-$(R_4Sn)$, tri-$(R_3SnX)$ or diorganotin halides $(R_2SnX_2)$ with $SnX_4$ to afford said monoorganotin trihalides in the presence of at least one transition metal complex, said complex comprising at least one transition metal M, selected from Group VIII of the periodic Table of elements, at least one monodentate ligand or bidentate ligand, L, L', or L", and optionally one or more anions, X, of an organic or inorganic acid, as a catalyst or catalyst precursor.

19 Claims, No Drawings

PROCESS FOR THE PRODUCTION OF MONOALKYLTIN TRIHALIDES

This application is the U.S. National Phase of International Application Number PCT/NL02/00045 filed on Jan. 21, 2002, which is incorporated herein by reference.

BACKGROUND OF THE INVENTION

The present invention concerns a transition metal-catalyzed process for the production of monoalkyltin trihalides involving a redistribution reaction between tetraorganotins, triorganotin halides or diorganotin halides and tin tetrahalides.

Monoalkyltin trichlorides can be prepared industrially from tetraalkyltins and $SnCl_4$ according to the stoichiometry of eq. 1 (Neumann, W. P.; Burkhardt, G. *Liebigs Ann. Chem.* 1963, 663, 11).

$$R_4Sn + 2\ SnCl_4 \rightarrow 2\ RSnCl_2 + R_2SnCl_2 \quad (1)$$

$$R_4Sn + 3\ SnCl_4 \rightarrow 4\ RSnCl_3 \quad (2)$$

$$R_2SnCl_2 + SnCl_4 \rightarrow 2\ RSnCl_3 \quad (3)$$

(R=alkyl or cycloalkyl)

This process was further improved by M&T chemicals (Natoli, J. G., U.S. Pat. No. 3,432,531, 1969; Larkin, W. A.; Bouchoux, J. W., U.S. Pat. No. 3,931,264, 1976). In this process substantial amounts of dialkyltin dichloride are formed as by-product (typically around 33%).

The reason that the process according to eq. 1 is often used and not that of eq. 2, is that eq. 3 does not proceed under mild conditions for longer alkyl groups. Eq. 3 would be the last step in a process according to eq. 2.

Nothwithstanding the above remarks, Neumann (U.S. Pat. No. 3,459,779, 1969) has described the redistribution reaction of dialkyltin halides with $SnCl_4$ in $POCl_3/P_2O_5$ to produce monoalkyltin trichlorides. Also Langer et al. reported the formation of $MeSnCl_3$ from dimethyltin dichloride and tin tetrachloride in dimethylsulfoxide (DMSO) (*Tetrahedron Lett.*, 1967, 1, 43–47; U.S. Pat. No. 3,454,610, 1969, to Dow Chemical Co.). Also the redistribution of dialkyltin dihalides, trialkyltin halides or tetraalkyltins with tin tetrahalide catalyzed by quarternary ammonium salts at temperatures above 150° C. has been reported (Kugele, T. G.; Parker, D. H., U.S. Pat. No. 3,862,198, 1975) and more recently, redistribution reactions of organotins catalyzed by $SnF_2$ were claimed by Buschhoff et al. (U.S. Pat. No. 4,604,475, 1986, to Schering A. G.).

All the processes described above generally use harsh reaction conditions and yields are often less than desirable.

It is therefore an object of the current invention to provide for a catalytic process for the production of monoorganotin trihalides from tetraalkyltins or polyalkyltin halides and tin tetrahalide that can be operated under mild conditions (T<150° C., p≦5 bar) and which affords the product in high yield (>60% based on Sn).

It is also an object of the current invention to make use of transition metal complexes as pre)catalyst as opposed to previously reported catalysts.

SUMMARY OF THE INVENTION

In its broadest form the present invention comprises a process for the production of monoalkyltin trihalides of the formula $RSnX_3$, wherein R=alkyl or cycloalkyl and X=Cl, Br or I, involving a redistribution reaction between tetraorganotins, triorganotin halides or diorganotin halides and tin tetrahalides, said process comprising contacting tetra-$(R_4Sn)$, tri-$(R_3SnX)$ or diorganiotin halides $(R_2SnX_2)$ with $SnX_4$ to afford said monoorganotin trihalides in the presence of at least one transition metal complex, said complex comprising at least one transition metal, M, selected from Group VIII of the periodic Table of elements, at least one monodentate ligand or bidentate ligand, L or L', and optionally one or more anions, X, of an organic or inorganic acid, as a catalyst or catalyst precursor.

According to one embodiment of the invention, the catalyst is based on the use of a complex having the formula $$L'MX_2 \quad (I)$$

wherein L' is a bidentate ligand, or $$L_2MX_2 \quad (II)$$

wherein L is a monodentate ligand, or $$L_4M \quad (III),$$

wherein L is a monodentate ligand.

According to another embodiment, the said complex is:

$$[L''M(\mu-X)]_2 \quad (IV)$$

wherein L''=a cyclometallated bidentate optionally substituted o-(diarylphosphino)benz-yl ligand. Catalysts of type (IV) have been applied for the Heck-vinylation of aryl halides (EP 725049 A1).

The metal to be used is a Group VIII metal, and preferred metals are Pt, Pd and/or Ni. The anions may be of organic and/or inorganic nature. It is preferred to use Cl, Br, I, acetate, triflate or tosylate anions.

The current invention thus involves the use of transition metal complexes according to formula (I), (II), (III), or (IV) as a (pre-)catalyst in the redistribution reaction of tetra-$(R_4Sn)$, tri-$(R_3SnX)$ or diorganotin halides $(R_2SnX_2)$ with $SnX_4$ to afford monoorganotin trihalides ($RSnX_3$; R=alkyl or cycloalkyl; X=Cl, Br or I).

In a preferred embodiment of the invention L in formula (II) or (III) is selected from phosphine, alkene, amine, organic sulfide, nitrile and imidazoline-2-ylidene. L' is selected from diphosphine, dialkene, diamine and bis (imidazoline-2-ylidene) ligands, preferably optionally substituted o-{di(2-tolyl)phosphino}benzyl. More in particular L is triphenylphosphine or L'=N,N,N',N'-tetramethylethylenediamine (TMEDA), M is Pd or Pt and for catalyst (I), X is Cl.

The catalyzed redistribution reaction concerns the redistribution of $Bu_2SnCl_2$ or $Bu_4Sn$ with $SnCl_4$ to afford $BuSnCl_3$. The use of (pre)catalysts according to formula (I), (II), (III) and (IV) allows the formation of $BuSnCl_3$ from redistribution of $Bu_2SnCl_2$ or $Bu_4Sn$ with $SnCl_4$ under mild reaction conditions (T≦150° C., p≦1 bar) in less than 24 hours and better than 70% yield (based on Sn).

The group R is preferably defined as an alkyl (linear or branched), cycloaryl or aryl, having from 1 to 12 C-atoms. Preferably methyl, n-butyl or n-hexyl are used.

The reaction can be carried out with or without a solvent. In general inert organic and aprotic solvents are preferred, especially aromatic solvents, chloroaromatics, alkanes, dialkylacetamides, N-alkylpyrolidones, dialkylamides of aliphatic carboxylic acids and organic nitriles. In particular toluene, o-xylene, 1,2-dichlorobenzene and n-octane were found to be appropriate solvents.

In a specific embodiment of the invention the concentration of the tin reagents employed falls within the range of 0.01 to 5, more preferred 0.1–2.0 M The catalyst loading based on the total amount of Sn used can be <5% and even <0.1%. The catalyst is preferably employed in the concentration range $5 \cdot 10^{-4}$–0.1 M.

In one specific example, which employed $PtCl_2(PPh_3)_2$ as catalyst (or catalyst precursor) in toluene at a reaction temperature of 85° C., the yield of $BuSnCl_3$ was found to be as high as 92% (based on Sn). $SnCl_2$ was the sole tin-containing by-product.

In another preferred embodiment of the invention the catalyzed redistribution reaction concerns redistribution between $R_2SnCl_2$ or $R_4Sn$ (R is Me, Et, propyl, hexyl, more preferably Me and n-hexyl) and $SnCl_4$ to afford $RSnCl_3$. For R=Me and n-hexyl, the monoalkyltin trichloride was obtained starting from $R_2SnCl_2$ and $SnCl_4$ in 87 and 67% yield, repectively, whereas in the blank experiment (no catalyst added) only unreacted starting materials were recovered.

The invention is now further demonstrated by the following examples.

EXAMPLES

Preparation of $BuSnCl_3$ from $Bu_2SnCl_2$ and $SnCl_4$ $Bu_2SnCl_2$ was either dissolved in the solvent or used as such. $SnCl_4$ was added followed by the catalyst. The reaction mixture was stirred for 12 h at 110° C. Filtration of the reaction mixture gave a slightly yellow solution which was analyzed by $^{119}Sn$ NMR using $SuMe_4$ as external standard. After evaporation of the solvent, butyltin trichloride was obtained as a colorless liquid by vacuum distillation (90° C./11 mmHg) and analyzed by $^1H$, $^{13}C\{^1H\}$ and $^{119}Sn\{^1H\}$ NMR spectroscopy. The solid material obtained from the filtration was washed with toluene (3×20 mL) and dried in vacuo to give an off-white solid which was identified as $SnCl_2$ by $^{119}Sn$ NMR ($\delta$=−235.1 in acetone-$d_6$) and/or elemental analysis. The results of the different experiments are presented in Table 1.

In one typical experiment, 373 g (1.32 mol, 80%) of $BuSnCl_3$ and 44.5 g (0.23 mol, 14%) of $SnCl_2$ were obtained starting from $Bu_2SnCl_2$ (252 g, 0.83 mol) in toluene (500 mL), $SnCl_4$ (215 g, 0.83 mol) and $PtCl_2(PPh_3)_2$ (215 mg, 0.27 mmol) as catalyst following the above procedure. Elemental analysis of $SnCl_2$: Cl, 37.0%; Sn, 61.23 %. $SnCl_2$ requires: Cl, 37.4%; Sn, 62.60%.

TABLE 1

Results of the reaction of $Bu_2SnCl_2$ with $SnCl_4$ (1:1 molar ratio) in the presence of several catalysts.[a]

| Entry | Catalyst | T (° C.) | [Catalyst] (mol %)[b] | Solvent[c] | Yield of $BuSnCl_3$ (%)[d] | Selectivity (%)[e] |
|---|---|---|---|---|---|---|
| 1 | $Pd(PPh_3)_4$ | 110 | 5 | no solvent | 60 (25) | n.d. |
| 2 | $PdCl_2(PPh_3)_2$ | 110 | 1 | no solvent | 64 | n.d. |
| 3 | $PdCl_2(TMEDA)$ | 110 | 5 | no solvent | 72 (70) | n.d. |
| 4 | $PtCl_2(PPh_3)_2$ | 110 | 0.1 | no solvent | 62 | n.d. |
| 5 | $PtCl_2(PPh_3)_2$ | 110 | 1 | toluene | 72 | n.d. |
| 6 | $PtCl_2(PPh_3)_2$ | 85 | 0.1 | toluene | 92[f] | 93[f] |
| 7 | $PtCl_2(PPh_3)_2$ | 110 | 0.1 | toluene | 84 (80) | 87 |
| 8 | $PtCl_2(PPh_3)_2$ | 130 | 0.1 | toluene | 85 | 86 |
| 9 | $PtCl_2(PPh_3)_2$ | 110 | 0.03 | toluene | n.d. (80) | n.d. |
| 10 | $PtCl_2(PPh_3)_2$ | 110 | 0.1 | o-xylene | 70 | 79 |
| 11 | $PtCl_2(PPh_3)_2$ | 110 | 0.1 | 1,2-dichlorobenzene | 85 | 83 |
| 12 | $PtCl_2(PPh_3)_2$ | 110 | 0.1 | n-octane | 76 | 89 |

[a]Reaction time = 12 h unless indicated otherwise.
[b]Relative tot $Bu_2SnCl_2$.
[c]$[Bu_2SnCl_2]_0 = [SnCl_4]_0 = 1.0$ M when toluene was used as solvent.
[d]Yield based on total amount of Sn, determined by $^{119}Sn$ NMR analysis of the crude reaction mixture. Isolated yield in brackets.
[e]By-product: $SnCl_2$
[f]After t = 48 h instead of 12 h.

Preparation of $MeSnCl_3$ from $Me_2SnCl_2$ and $SnCl_4$.

In this typical experiment, 3.40 g (14.1 mmol, 87%) of $MeSnCl_3$ was obtained starting from $Me_2SnCl_2$ (1.80 g, 8.3 mmol) in toluene (5 mL), $SnCl_4$ (1.0 mL, 8.3 mmol) and $PtCl_2(PPh_3)_2$ (6.5 mg, 8.2 μmol) as catalyst following the above procedure for preparation of $BuSnCl_3$. After filtration volatiles were removed in vacuo (1 mm Hg) to afford the product as a white solid. No $SnCl_2$ formation was observed.

Preparation of $(n-C_6H_{13})SnCl_3$ from $(n-C_6H_{13})_2SnCl_2$ and $SnCl_4$.

In this typical experiment, 1.15 g (3.70 mmol, 67%) of $(n-C_6H_{13})SnCl_3$ was obtained starting from $(n-C_6H_{13})_2SnCl_2$ (1.0 g, 2.78 mmol) in toluene (10 mL), $SnCl_4$ (0.72 g, 2.78 mmol) and $PtCl_2(PPh_3)_2$ (23 mg, 27.8 μmol) as catalyst following the above procedure for preparation of $BuSnCl_3$. After filtration volatiles were removed in vacuo (2 mm Hg) and the remaining liquid was vacuum-transferred (ca 200° C., 1–2 mm Hg). $SnCl_2$ (0.23 g, 1.2 mmol, 21%) was isolated as side-product.

Preparation of $BuSnCl_3$ from $Bu_4Sn$ and $SnCl_4$.

In this typical procedure, $SnCl_4$ (11.15 g, 0.043 mol) was dissolved in toluene (10 mL). Next, $Bu_4Sn$ (4.96 g, 0.0143 mol) was added and reaction mixture was stirred for 2 h at 110° C. After cooling of the reaction mixture to room temperature, the catalyst $PtCl_2(PPh_3)_2$ (3.8 mg, 4.8 μmol) was added and the reaction mixture was stirred for another 12 h at 110° C. Filtration of the reaction mixture gave a slightly yellow solution which was analyzed by $^{119}Sn$ NMR using $SnMe_1$ as external standard. After evaporation of volatiles in vacuo, vacuum distillation (90° C./11 mmHg) afforded 13.5 g (83%) of butyltin trichloride as a colorless liquid. The solid material obtained from the filtration was washed twice with toluene (5 mL) and dried in vacuo to give 0.40 g of an off-white solid. The solid was dissolved in acetone-$d_6$ and in identified as $SnCl_2$ by $^{119}Sn$ NMR ($\delta$=−235.1). Elemental analysis: Cl, 36.92%; Sn, 62.40%. $SnCl_2$ requires: Cl, 87.40%; Sn, 62.60%. The results of the different experiments are presented in Table 2.

TABLE 2

Results of the reaction of $Bu_4Sn$ with $SnCl_4$ (1:3 molar ratio) in the presence of several catalysts.[a]

| Entry | Catalyst | [Catalyst] (mol %)[b] | Solvent[c] | Yield of $BuSnCl_3$ (%)[d] |
|---|---|---|---|---|
| 1 | $Pd(PPh_3)_4$ | 5 | toluene | n.d. (47) |
| 3 | $PdCl_2(PPh_3)_2$ | 1 | no solvent | n.d. (72) |
| 4 | $PtCl_2(PPh_3)_2$ | 0.1 | toluene | 77 (75) |
| 5 | $PtCl_2(PPh_3)_2$ | 0.03 | toluene | 87 (83) |
| 6 | — | | no solvent | n.d. (63)[e] |

[a]Conditions: T = 110° C., t = 12 h.
[b]Relative to $Bu_4Sn$.
[c]$[SnCl_4]_0$ = 1.0 M when toluene was used as solvent.
[d]Yield based on Sn, determined by $^{119}Sn$ NMR analysis of the crude reaction mixture. Isolated yield in brackets.
[e]$Bu_4Sn:SnCl_4$ = 1:2.
n.d. = not determined

What is claimed is:

1. Process for the production of monoalkyltin trihalides of the formula $RSnX_3$, wherein R=alkyl or cycloalkyl and X=Cl, Br or I, involving a redistribution reaction between tetraorganotins, triorganotin halides or diorganotin halides and tin tetrahalides, said process comprising contacting tetra- ($R_4Sn$), tri- ($R_3SnX$) or diorganotin halides ($R_2SnX_2$) with $SnX_4$ to afford said monoorganotin trihalides in the presence of at least one transition metal complex, said complex comprising at least one transition metal, M, selected from Group VIII of the periodic Table of elements, at least one monodentate ligand or bidentate ligand, L or L', and optionally one or more anions, X, of an organic or inorganic acid, as a catalyst or catalyst precursor.

2. Process according to claim 1, wherein the said complex has the formula $$L'MX_2 \quad (I)$$

wherein L' is a bidentate ligand, or $$L_2MX_2 \quad (II)$$

wherein L is a monodentate ligand, or $$L_4M \quad (III)$$

wherein L is a monodentate ligand.

3. Process according to claim 1, wherein the said complex has the formula $$[L''M(\mu\text{-}X)]_2 \quad (IV)$$

wherein L''=a cyclometallated bidentate optionally substituted o- (diarylphosphino)benzyl ligand.

4. Process according to claim 1, wherein M is selected from Pt, Pd and Ni.

5. Process according to claim 1, wherein X is selected from Cl, Br, I, acetate, triflate and tosylate anion.

6. Process according claim 1, wherein L is selected from phosphine, alkene, amine, organic sulfide, nitrile and imidazoline-2-ylidene.

7. Process according to claim 1, wherein L' is selected from diphosphine, dialkene, diamine and bis(imidazoline-2-ylidene) ligands.

8. Process according to claim 3, wherein L'' is an optionally substituted o-{di(2-tolyl)phosphino}benzyl.

9. Process according to claim 1, wherein the catalyst, catalyst precursor or catalyst system is formed by combining (I), (II) or (III) with another ligand L selected from phosphine, alkene, amine, organic sulfide, nitrile and imidazoline-2-ylidene.

10. Process according to claim 1, wherein said monodentate ligand L is defined as a triarylphosphine, more preferably triphenylphosphine.

11. Process according to claim 1, wherein said bidentate ligand L' is defined as a bidentate nitrogenligand, more preferably N,N,N',N'-tetramethylethylenediamine (TMEDA).

12. Process according to claim 1, wherein R is selected from the group of alkyls having 1–12 carbon atoms.

13. Process according to claim 1, wherein the reaction is carried out in the presence of a solvent, said solvent preferably being selected from the group of aromatic solvents, chioroaromatics, alkanes, dialkylacetamides, N-alkylpyrolidones, dialkylamides of aliphatic carboxylic acids and organic nitriles.

14. Process to claim 1, wherein M is Pt and/or Pd.

15. Process according to claim 1, wherein X is Cl.

16. Process according to claim 1, wherein the reaction is carried out at a temnerature between 0 and 200 0C.

17. Process according to claim 1, wherein the reaction is carried out at a pressure between 1 and 5 bar.

18. Process according to claim 1, wherein the monoalkyltin trihalide product is obtained in >60% yield (based on Sn) in less than 49 h at temperatures below 150 0C.

19. A method of using a transition metal complex comprising at least one transition metal, M, selected from Group VIII of the periodic Table of elements, at least one monodentate ligand or bidentate ligand, L, L' or L'', and optionally one or more anions, X, of an organic or inorganic acid, as a catalyst or catalyst precursor for the production of monoalkyltin trihalides of the formula $RSnX_3$, wherein R alkyl or cycloalkyl and X=Cl, Br or I, using a redistribution reaction between tetruorganotins, triorganotin halides or diorganotin halides and tin tetrahalides.

* * * * *

UNITED STATES PATENT AND TRADEMARK OFFICE
CERTIFICATE OF CORRECTION

PATENT NO. : 6,768,017 B2
DATED : July 27, 2004
INVENTOR(S) : Thoonen et al.

Page 1 of 1

It is certified that error appears in the above-identified patent and that said Letters Patent is hereby corrected as shown below:

Column 2,
Line 3, now reads "diorganiotin" should read -- diorganotin --.
Line 56, now reads "cycloaryl or aryl", should read -- cycloalkyl or aryl --.

Column 3,
Line 53, now reads "of $BuSnCl_2$ from" should read -- of $BuSnCl_3$. from --.
Line 57, now reads "$SuMe_4$" should read -- $SnMe_4$ --.

Column 5,
Line 3, now reads "Cl, 87.40%" should read -- Cl, 37.40% --.

Column 6,
Line 30, now reads "chioroaromatics" should read -- chloroaromatics --.
Line 36, now reads "temnerature between 0 and 200 0C" should read -- temperature between 0 and 200º C --.
Line 41, now reads "150 0C" should read -- 150ºC --.
Line 48, now reads "R alkyl" should read -- R=alkyl --.
Line 50, now reads "tetruorganotins" should read -- tetraorganotins --.

Signed and Sealed this

First Day of February, 2005

JON W. DUDAS
*Director of the United States Patent and Trademark Office*